(12) United States Patent
Uchihara et al.

(10) Patent No.: US 6,516,654 B2
(45) Date of Patent: Feb. 11, 2003

(54) APPARATUS AND METHOD FOR ANALYZING PARTICULATE MATTER IN GAS AND APPARATUS AND METHOD FOR CARBON DIFFERENTIATING

(75) Inventors: Hiroshi Uchihara, Kyoto (JP); Junji Okayama, Kyoto (JP); Atsushi Bando, Kyoto (JP); Masahiko Ikeda, Kyoto (JP); Masayuki Adachi, Kyoto (JP); Ichiro Asano, Kyoto (JP); Hirokazu Fukushima, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/730,361

(22) Filed: Dec. 5, 2000

(65) Prior Publication Data

US 2001/0029775 A1 Oct. 18, 2001

(30) Foreign Application Priority Data

Dec. 10, 1999 (JP) .......................................... 11-351067
Mar. 29, 2000 (JP) ....................................... 2000-092283
Aug. 30, 2000 (JP) ....................................... 2000-261344

(51) Int. Cl.$^7$ .......................... G01N 1/00; G01N 15/00; G01N 21/72
(52) U.S. Cl. ..................... 73/28.04; 73/28.01; 436/155; 436/157; 436/160
(58) Field of Search .......................... 73/28.01, 28.02, 73/28.04, 31.07; 436/155, 157, 160

(56) References Cited

U.S. PATENT DOCUMENTS

| | | | |
|---|---|---|---|
| 3,731,539 A | 5/1973 | Brittan et al. ................ | 422/100 |
| 3,861,874 A | 1/1975 | Krc ............................... | 422/80 |
| 4,519,983 A | 5/1985 | Espitalie et al. .............. | 422/78 |
| 4,759,210 A | 7/1988 | Wohltjen ...................... | 422/88 |
| 5,110,747 A | 5/1992 | Pataschnick et al. ......... | 110/217 |
| 5,204,270 A | 4/1993 | LaCount ...................... | 250/343 |
| 5,279,146 A | 1/1994 | Asano et al. ................. | 422/83 |
| 5,279,970 A | 1/1994 | Patashnick et al. .......... | 110/217 |
| 5,338,515 A | 8/1994 | Dalla Betta et al. ......... | 23/293 S |
| 5,550,062 A | 8/1996 | Wohltjen et al. ............. | 436/155 |

*Primary Examiner*—Hezron Williams
*Assistant Examiner*—Michael Cygan
(74) *Attorney, Agent, or Firm*—Oppenheimer Wolff & Donnelly LLP; Brian F. Swienton

(57) ABSTRACT

The present invention provides a method for analyzing particulate matter in a gas for analyzing simply and with high precision the particulate matter in an engine emission and an apparatus therefor by which dry soot, SOF and sulfate in PM contained in an engine emission can be fractionated individually even in a trifle amount. The present invention further provides a carbon differentiating and analyzing apparatus capable of differentiating and analyzing with precision the organic carbon and the elemental carbon contained in a sample and capable of performing a predetermined analysis with precision in a short time by reducing the period of time required for the analysis. The present invention is constituted such that a heating furnace is provided with a filter which has caught PM contained in engine emission. The filter is heated at a predetermined temperature while passing an inert gas into the heating furnace to evaporate the SOF and sulfate contained in PM. The evaporated SOF is oxidized into $CO_2$ and the evaporated sulfate is reduced into $SO_2$. The $CO_2$ and $SO_2$ are analyzed with a gas analyzer unit, and thereafter, the filter is heated while passing oxygen into the heating furnace to oxidize the PM remaining on the filter to have it generate $CO_2$. The $CO_2$ is analyzed with the gas analyzer unit. The present invention is constituted such that a thermal decomposition tube includes, successively from its upstream side a carrier gas inlet, a low temperature heating portion for evaporating organic carbon in the sample, and a high temperature heating portion for thermally decomposing elemental carbon in the sample, whereby the organic carbon is separated in the low temperature heating portion and the elemental carbon is separated in the high temperature heating portion.

7 Claims, 11 Drawing Sheets

APPARATUS AND METHOD FOR ANALYZING PARTICULATE MATTER IN GAS AND APPARATUS AND METHOD FOR CARBON DIFFERENTIATING

FIELD OF THE INVENTION

The present invention relates to an apparatus and method for analyzing particulate matter (hereinafter referred to as PM) contained in a gas discharged, for example, from diesel engine. The present. invention further relates to a carbon differentiating and analyzing apparatus and method capable of differentiating and analyzing organic carbon and elemental carbon contained in a sample.

DESCRIPTION OF THE PRIOR ART

As a procedure for determining PM contained in an emission of diesel engine, there is known in general a filter weighing method for quantitative analysis based on the weight difference from the filter before capturing PM which comprises diluting a high temperature emission discharged from the diesel engine with clean air, capturing PM with a filter by inhaling the diluted emission by a fixed capacity, and weighing the filter with a precision balance or the like.

However, in the above filter weighing method, the large effect of water content absorbed by the filter leads to measurement error. Constant temperature and constant moisture processing is required to maintain the water content at a constant in the filter before and after capture. Furthermore, in determining the emission of low concentration PM, it is necessary to weigh accurately PM of 0.1 mg captured on a filter of for example 200 mg. Thus, there is a problem such that the measurement error of the weight of the filter itself gives a significant effect on the measurement error of the PM weight.

Against the above, as shown in U.S. Pat. Nos. 5,110,747, 5,196,170, 5,279,970, and 5,401,468 publications, there is a procedure of heating a filter which has captured PM in a heating furnace by elevating the temperature stepwise, oxidizing PM, and determining PM with a gas analyzer.

However, the majority of PM is constituted by the inorganic carbon called dry soot (hereinafter, to be dry soot), hydrocarbon called SOF (soluble organic fraction) (hereinafter, to be SOF), and sulfuric acid hydrate called sulfate (hereinafter, to be sulfate), and depending on the procedure described in the above publication, separation of high boiling SOF and reduction of sulfate in an oxidation atmosphere are difficult. Accordingly, it has been difficult to measure individually the concentration or weight of the dry soot, SOF and sulfate by separating them which occupy the majority part in PM.

The present invention has been made in consideration of the matters described above, and its object is to provide a method for analyzing simply and with high precision the particulate matter in an engine emission and an apparatus therefor by which dry soot, SOF and sulfate in PM contained in an engine emission can be fractionated individually even when in a minute amount.

Further, elemental carbon, which is one of the carbon components contained in TSP (total suspended particulate matter) in atmospheric air, is involved in the oxidation of $SO_2$ into $SO_4^{2-}$, and may cause climatic change depending on its concentration. One technique for analyzing the elemental carbon is to thermally separate between elemental carbon and organic carbon, which is the other carbon component contained in TSP.

FIG. 11 is a schematic view showing a construction of a conventional carbon differentiating and analyzing apparatus. Referring to FIG. 11, a thermal decomposition tube 61 includes, on one end, a sample entrance 62 having a lid freely openable and closable for inserting a sample S, and on the other end, a gas exit 63. The thermal decomposition tube 61 further includes, on the sample entrance 62 side thereof (hereafter to be referred to as upstream side), an inlet 64 of carrier gas CG. A heater 65 is wound around the outer circumference of the thermal decomposition tube 61 on the downstream side of the carrier gas inlet 64, and the temperature of the heater 65 can be set to both a low temperature and a high temperature. A $CO_2$ analyzer 66 is connected to the gas exit 63 via a suitable passageway (not illustrated). Further, the sample S is mounted on a sample boat 67.

Operation of the carbon differentiating and analyzing apparatus having the aforesaid construction will be described. First, a sample boat 67 having a sample S mounted thereon is set at a predetermined position in the thermal decomposition tube 61. In this state, the heater 65 is set at a low temperature (for example, about 400° C.) to heat the sample S, whereby the organic carbon contained in the sample S is evaporated to become $CO_2$ and then carried to the $CO_2$ analyzer 66 by the carrier gas CG to be measured for $CO_2$ concentration. Next, the heater 65 is set at a high temperature (for example, about 1000° C.) to further heat the sample S, whereby the elemental carbon contained in the sample S is thermally decomposed to become $CO_2$ and then carried to the $CO_2$ analyzer 66 by the carrier gas CG to be measured for $CO_2$ concentration. Based on the $CO_2$ concentration obtained in each of the aforesaid measurements, the amount of the organic carbon and the amount of the elemental carbon in the sample S can be determined.

However, in the case of the aforesaid conventional carbon differentiating and analyzing apparatus, only a single heater 65 is used. Thus, it takes time to set the heater 65 from a low temperature to a high temperature, and further time is needed to set the heater 65 from a high temperature to a low temperature. Moreover, since it is difficult to detect the HC component evaporating at a low temperature with the use of the $CO_2$ analyzer, a HC gas sensor is further needed. Also, CO is generated to cause errors if the oxidation does not sufficiently takes place because of insufficient temperature.

The present invention has been made in order to take the above-mentioned matters into account. An object thereof is to provide a carbon differentiating and analyzing apparatus capable of differentiating and analyzing, with precision, the organic carbon and the elemental carbon contained in a sample, and capable of performing a predetermined analysis with high precision in a short time by reducing the period of time required for analysis.

SUMMARY OF THE INVENTION

In order to attain the above object, the method for analyzing PM in gas of the present invention comprises providing a filter which has caught PM contained in engine emission in a heating furnace, firstly heating the filter at a predetermined temperature while passing an inert gas into a heating furnace to evaporate the SOF and sulfate. contained in PM, oxidizing the evaporated SOF into $CO_2$ and reducing the evaporated sulfate into $SO_2$, analyzing the $CO_2$ and $SO_2$ with a gas analyzer unit, and thereafter, heating the filter while passing oxygen into the heating furnace to oxidize the PM remaining on said filter to have it generate $CO_2$, and analyzing the $CO_2$ with the gas analyzer unit.

As a concrete apparatus for executing the above analyzing method, there is used in the present invention an apparatus comprising a gas feeder for selectively feeding an inert gas or oxygen to a heating furnace, a heating furnace for heating at a predetermined temperature a filter which has captured the PM contained in the engine emission in a condition where the inert gas or oxygen is fed, an oxidation reduction processor for oxidizing or reducing the gas generated by heating, and a gas analyzer unit for determining the concentrations of CO and SO under supply of a gas from the oxidation reduction processor.

According to the method for analyzing particulate matter in gas of the present invention, a filter is installed in a flow passage in which an emission from an engine is passed. The emission is passed at a predetermined flow amount and the PM in the emission is captured by a filter. The filter is provided in a heating furnace which is maintained for example at 1000° C. Firstly, the filter is heated while an inert gas such as nitrogen gas is passed into the heating furnace to gasify SOF and sulfate in PM, and the evaporated SOF is oxidized into $CO_2$ and the evaporated sulfate is reduced into $SO_2$. Then, the $CO_2$ and $SO_2$ are analyzed with a gas analyzer unit to obtain the $CO_2$ concentration and $SO_2$ concentration. The $CO_2$ concentration and $SO_2$ concentration are proportionate to the amount of the SOF and the sulfate in PM, respectively. From the $CO_2$ concentration and $SO_2$ concentration and the total flow amount of the inert gas, the weight of $CO_2$ and $SO_2$ are obtained. Based on the weight of $CO_2$ and $SO_2$, the weight of SOF and sulfate captured by the filter are obtained.

Subsequently, while flowing oxygen into the heating furnace, the filter is heated to oxidize the PM remaining on the filter (major part is dry soot) to generate $CO_2$, and the $CO_2$ is analyzed by the gas analyzer unit to obtain the $CO_2$ concentration. The $CO_2$ concentration is proportional to the amount of the dry soot in PM, and the weight of $CO_2$ is obtained from the $CO_2$ concentration and the total flow of oxygen. Based on the weight of $CO_2$, the weight of the dry soot captured by the filter is obtained.

In the above method for analyzing PM in the gas, the filter is heated by passing an inert gas into the heating furnace. Firstly, low temperature heating is effected to an extent that the SOF of low boiling temperature is evaporated. Thereafter, high temperature heating is effected to an extent that the SOF of high boiling temperature is evaporated. When such practice is performed, determination can be made by distinguishing between the high boiling point SOF and the low boiling point SOF.

Further, in the aforesaid method of analyzing the PM contained in the gas, the aforesaid sulfate may be passed through heated quartz fibers to reduce the evaporated sulfate into $SO_2$. If this is carried out, the sulfate can be heated efficiently and with certainty so that the sulfate can be reduced to $SO_2$ with more certainty.

Further, in order to achieve the aforesaid object, the present invention provides a carbon differentiating and analyzing apparatus including a thermal decomposition tube having a sample entrance formed at one end and a gas exit formed at the other end. A $CO_2$ analyzer is connected to the gas exit side, wherein the thermal decomposition tube includes, successively from its upstream side, a carrier gas inlet, a low temperature heating portion for evaporating organic carbon in the sample, and a high temperature heating portion for thermally decomposing elemental carbon in the sample, whereby the organic carbon is separated in the low temperature heating portion and the elemental carbon is separated in the high temperature heating portion.

The aforesaid carbon differentiating and analyzing apparatus eliminates the time required for heating and cooling during carbon differentiation and analysis.

A high temperature oxidizing portion is provided midway between the high temperature heating portion and the gas exit for oxidizing generated carbon compounds such as HC and CO into $CO_2$, HC and CO prevented from flowing into the $CO_2$ analyzer as they are.

Also, if a tube for introducing oxygen or air is connected at a site between the high temperature heating portion and the high temperature oxidizing portion of the thermal decomposing tube, low temperature CO in the presence of oxygen is completely converted into $CO_2$, whereby errors of the $CO_2$ analyzer caused by the generation of CO can be eliminated.

Furthermore, if the tube for introducing oxygen or air and a neighborhood of a site of connection between the tube and the thermal decomposition tube are heated, the temperature of gas generated by introduction of oxygen or air is prevented from decreasing, and the $CO_2$ concentration can be measured with a higher precision.

Still further, if a switching valve is provided at a site between the gas exit of the thermal decomposition tube and the $CO_2$ analyzer, gases that should not flow into the $CO_2$ analyzer, such as air flowing in from the outside and gas that is passed for purging the inside of the thermal decomposition tube, can be discharged to the outside.

DETAILED DESCRIPTION OF THE PREFERRED EMBODIMENTS

Figure 1:
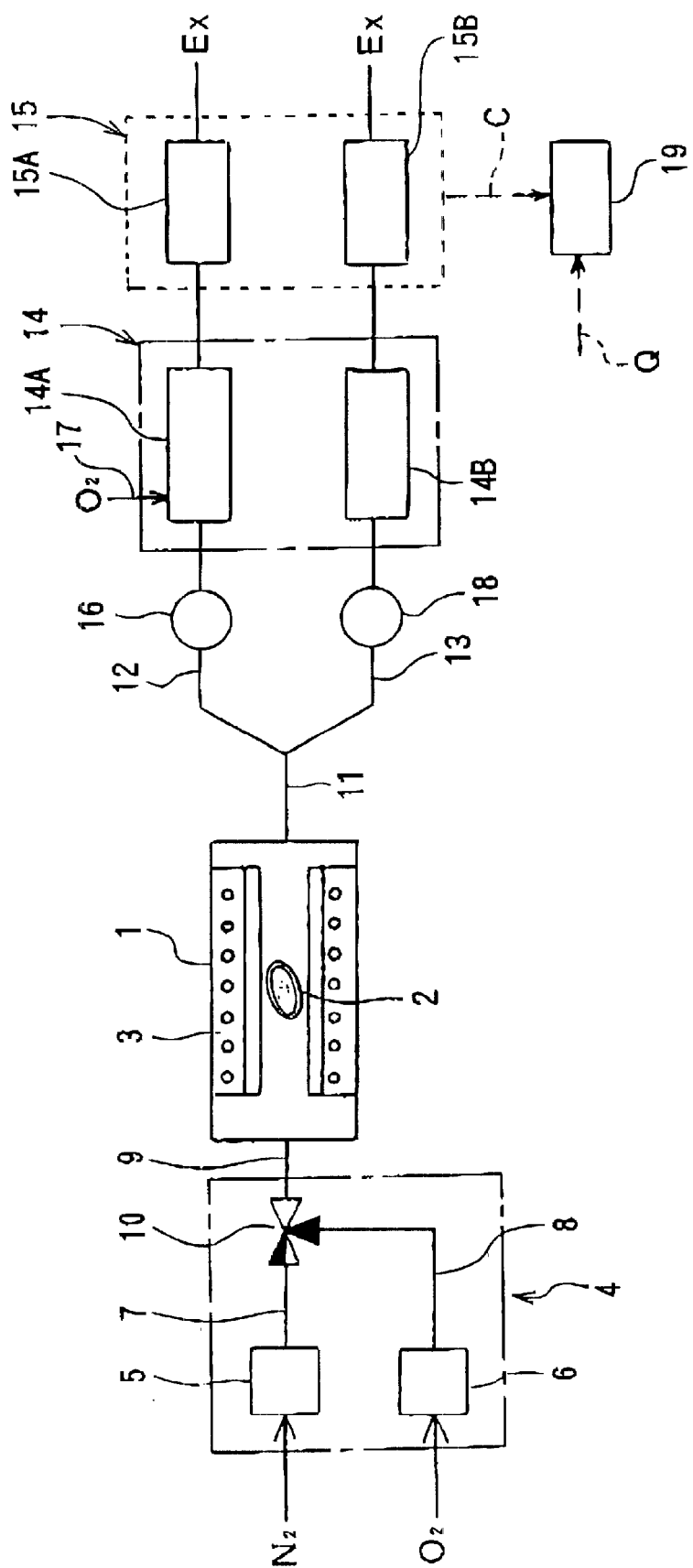
FIG. 1 is a view schematically showing an exemplary embodiment of an apparatus for analyzing particulate matter in a gas in accordance with the present invention.

An embodiment of the present invention is explained with reference to FIG. 1 and FIG. 2. FIG. 1 schematically shows a constitution example of an apparatus for analyzing the particulate matter in the gas. Reference numeral 1 denotes a heating furnace for heating a filter 2 (the constitution for capturing PM will be described later) which has captured PM from the engine emission, comprising for example an electric furnace, which is equipped with a heater 3 for heating. The heater 3 for heating undergoes control of heating condition thereof by means of the temperature adjusting mechanism (not illustrated), and accordingly the temperature in the heating furnace 1 is set to be the optional predetermined temperature.

Reference numeral 4 denotes a gas feeder for selectively feeding an inert gas (e.g., nitrogen gas) or oxygen to a heating furnace 1. The gas feeder 4 is constituted by a nitrogen gas feeding passage 7 and an oxygen feed passage 8 respectively furnished with the flow controller 5, 6 such as mass flow controllers having the functions of flow determination and flow control. The downstream side of the feed passages 7, 8 are connected to a three-way electromagnetic valve 10, and the downstream side of a connection flow passage 9 is connected to the heating furnace 1.

Reference numeral 11 denotes a gas flow passage through which the gas generated in the heating furnace 1 is passed. The downstream side is branched into the two parallel gas flow passages 12, 13. The downstream side of the gas flow passages 12, 13, is provided in series an oxidation reduction processor 14 and a gas analyzer unit 15, in this order.

More particularly, one gas flow passage 12 includes a flow meter 16 such as a mass flow meter, an oxygen feed passage 17 for feeding oxygen connected oxidation processor 14A having oxidized catalyst such as CuO, and a $CO_2$ analyzer 15A, in this order. The other gas flow passage 13 includes a flow meter 18 similar to the above flow meter 16, a reducing processor 14B having reducing catalyst such as carbon, and an $SO_2$ analyzer 15B, in this order. The $CO_2$ analyzer 15A and $SO_2$ analyzer 15B to be used here are, for example, non-dispersion type infrared gas analyzers (NDIR gas analyzers). That is to say, in the oxidation reduction processor 14, the oxidation processor 14A and the reduction processor 14B are disposed in parallel with each other, and in the gas analyzer unit 15, the $CO_2$ analyzer 15A and $SO_2$ analyzer 15B are disposed in parallel with each other.

Now, though not illustrated, the gas flow passages 9, 11 and the portions up to the gas analyzer unit 15 of the gas flow passages 12, 13 (including the oxidation processor 14A and reduction processor 14B) are constituted so as to be heated and to retain heat to maintain a suitable temperature by heater, etc. This is in order to prevent the change in the components contained in the gas formed in the heating furnace 1 and to insure oxidation and reduction processing.

Reference numeral 19 denotes an operation controller for performing operation based on the signals (flow signal Q, concentration signal C, etc.) from various parts of apparatus or sending out control signals to various parts of apparatus based on the results of the operation, comprising for example a personal computer.

The above filter 2 comprises, for example, quartz having less impurities. In order to have the filter 2 capture PM contained in engine emission, there is used for example a sampling apparatus which is constituted as shown in FIG. 2 and is capable of passing a fixed flow amount of the emission from the engine. Namely, in FIG. 2, reference numeral 20 denotes, for example, a diesel engine loaded on an automobile, and reference numeral 21 denotes an exhaust pipe connected therewith. Reference numeral 22 denotes a probe inserted into the exhaust pipe 21 for sampling the emission G which flows in the exhaust pipe 21, and its downstream side is connected to the dilution tunnel 23 for diluting the sampled emission G. Reference numeral 24 denotes a pipe for feeding air for dilution to be connected to the upstream side of the dilution tunnel 23.

Reference numeral 25 denotes a gas flow passage for passing the diluted sample gas S connected to the downstream side of the dilution tunnel 23. The downstream side of the flow passage 25 is branched into two flow passages 26, 27. The respective flow passages 26, 27 are provided with the filters 28, 29 for capturing PM contained in the sample gas S, so that one flow passage 26 is constituted into a sample gas flow passage and the other flow passage 27 into a bypass flow passage for passing the emission when not sampling the PM, respectively. Of the filters 28, 29, one filter 28 is a filter for measurement, and the other filter 29 is a dummy filter.

Reference numeral 30 denotes a three-way electromagnetic valve as flow passage changeover means provided on the downstream sides of the sample gas flow passage 26 and bypass flow passage 27. The downstream side of the three-way electromagnetic valve 30 is connected to the gas flow passage 31. The gas flow passage 31 is provided with a suction pump whose suction capacity can be varied by controlling the number of revolutions, e.g., Roots blower pump 32 and a flow meter having high measurement precision, e.g., a venturimeter in this order.

Figure 3:
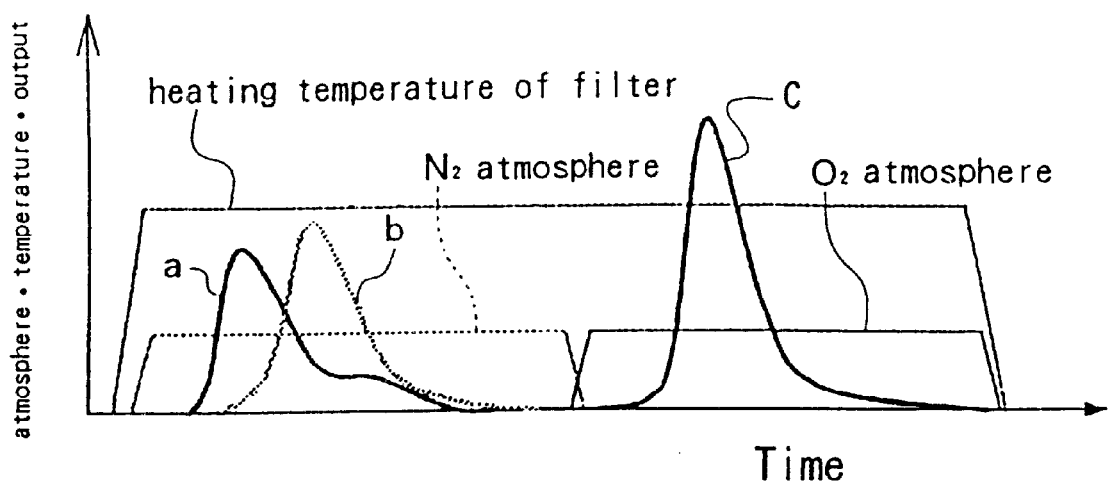
FIG. 3 is a view illustrating the motion of the present invention.

Next, a method for analyzing the particulate matter using the analyzer of the particulate matter in gas having the above constitution is explained with reference to FIG. 3 as well. FIG. 3 shows the change in time of the atmosphere in the heating furnace 1 and the heating temperature of the filter 2 and the condition of the output in each atmosphere. The marks a, c denote the $CO_2$ concentration outputs, and b shows the $SO_2$ concentration output.

Figure 2:
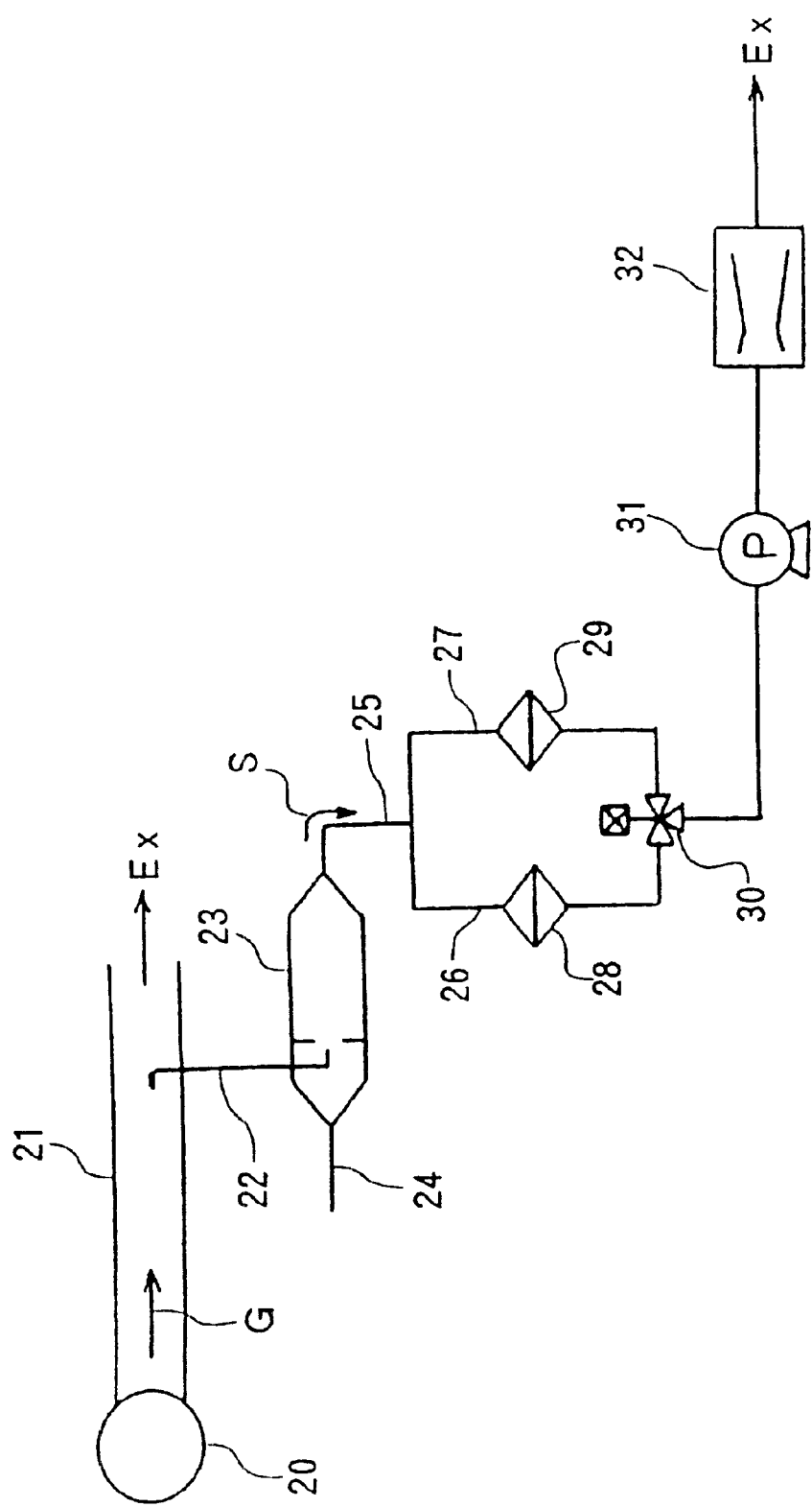
FIG. 2 is a view to show schematically an example of the sampling apparatus for having the filter capturing PM.

At first, prior to the analysis, using a sampling apparatus shown in FIG. 2, emission G from the engine 20 is sampled by a fixed flow volume and PM in the emission G is captured on the filter 2.

Referring again to FIG. 1, the filter 2 which has captured PM is placed in the heating furnace 1 which is heated in advance to make the inside temperature 1000° C. At first, the electromagnetic valve 10 of the gas feeder 4 is actuated to make the nitrogen gas feeding passage 7 communicate with the heating furnace 1 to feed nitrogen gas into the heating furnace 1 through a flow controller 5. The flow amount of the nitrogen gas at this time is measured by the flow controller 5, and the results thereof are sent to the personal computer 19 as a flow signal Q.

In the above heating furnace 1, the filter 2 is heated at 1000° C. in a nitrogen gas atmosphere, by which the SOF and sulfate in the PM captured by the filter 2 are gasified. The gasified SOF and Sulfate flow out into the gas flow passage 11 along with the nitrogen gas.

The gas sent out through the gas flow passage 11 (containing the gasified SOF and sulfate and other generated gases) flows in the gas flow passages 12, 13 under the condition of being divided into two equal parts. And, the gas which flows in one gas flow passage 12 passes into the oxidation processor 14A of the oxidation reduction processor 14 through the flow meter 16. Oxygen is supplied to the oxidation processor 14A, wherein the SOF out of the gasified SOF and sulfate is oxidized by the oxidized catalyst and oxygen to become $CO_2$ and $HO_2$, which, together with other gases, are sent to the $CO_2$ analyzer 15A of the gas analyzer unit 15, and their $CO_2$ concentration is measured. Also, the gas which flows through the other gas flow passage 13 runs into the reduction processor 14B of the oxidation reduction processor 14 through the flow meter 18, in which the sulfate out of the evaporated SOF and sulfate is reduced by the reducing catalyst to become $SO_2$, which is sent together with other gases to the $SO_2$ analyzer 15B of the gas analyzer unit 15 and $SO_2$ concentration is measured.

Figure 4:
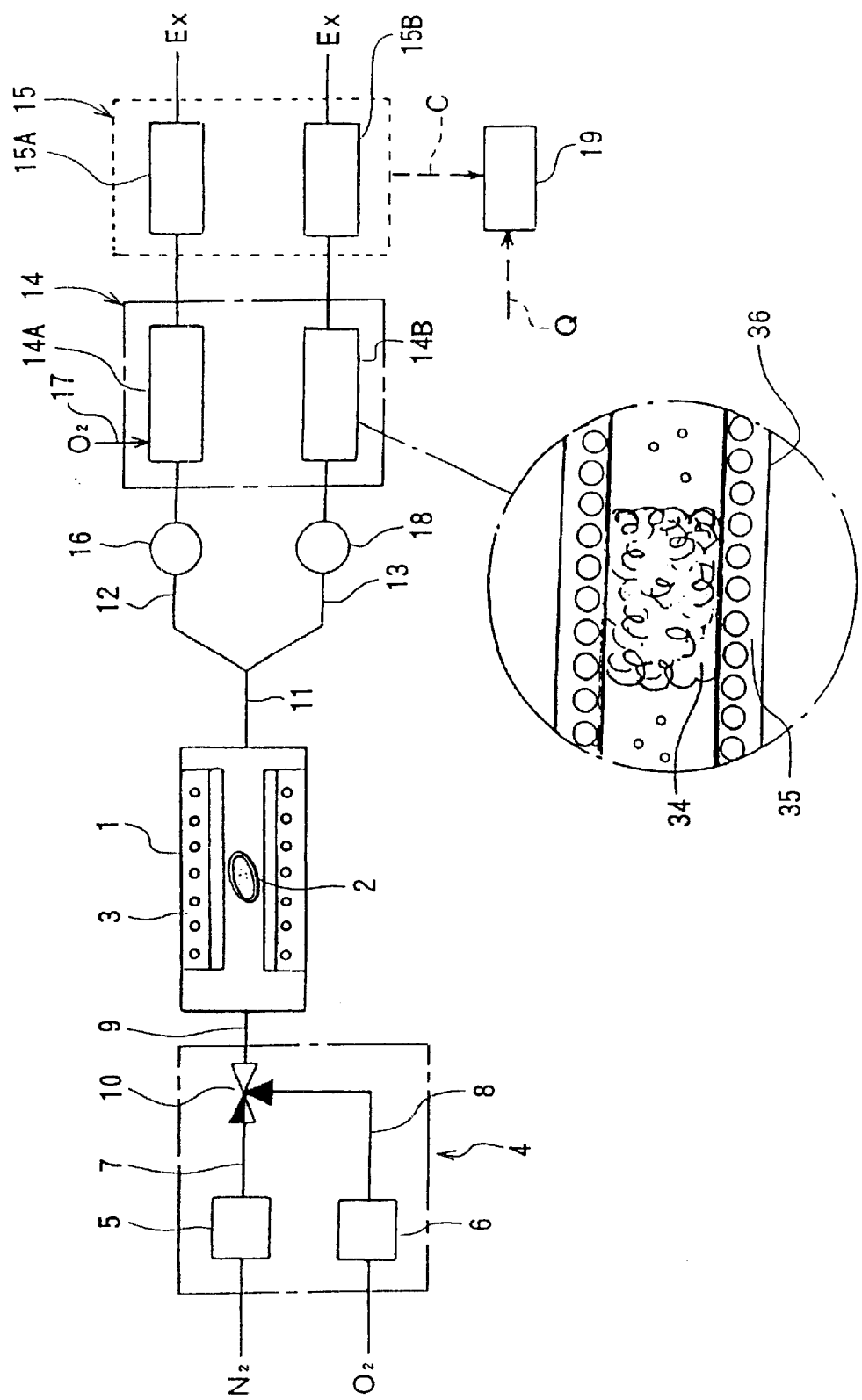
FIG. 4 is a view schematically showing another embodiment of the reduction processing portion according to the present invention.

Here, referring to FIG. 4, reduction of sulfates into SO may be promoted by disposing quartz fibers 34 instead of disposing a reduction catalyst in the aforesaid reduction processing part 14B and passing the sulfates through the quarts fibers 34.

In other words, $SO_3$ is obtained by evaporating the sulfates, and by heating the $SO_3$, the following reaction takes place:

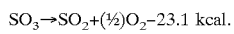

$$SO_3 \rightarrow SO_2 + (\frac{1}{2})O_2 - 23.1 \text{ kcal.}$$

Here, the sulfates are not sufficiently heated by simply passing the sulfates through the inside of the tube 36 heated by the heater 35, and there is a fear that the sulfates may be sent to the analyzer 15B without being reduced into $SO_2$. However, if the quartz fibers are disposed in the reduction processing part 14B as mentioned above and heated by a heater in advance and if the sulfates are passed through the heated quartz fibers, then the heat from the tube wall is efficiently transmitted to the sulfates by the quartz fibers when the sulfates pass through the quartz fibers, whereby the sulfates can be heated efficiently and with certainty, and the reduction to $SO_2$ can be carried out with more certainty. This makes it possible to measure the sulfates in the PM with precision. Needless to say, it is possible to adopt a construction in which both the reduction catalyst and the quartz fibers are disposed in the aforesaid reduction processing part 14B.

The gas analyzer unit 15 outputs the $CO_2$ concentration and $SO_2$ concentration switched of the configurations as shown for example in the marks a, b in FIG. 3. The $CO_2$ concentration and $SO_2$ concentration signals are inputted to the personal computer 19. As the signal to represent the flow of the nitrogen gas is inputted into the personal computer 19, based on the nitrogen gas flow, $CO_2$ concentration and $SO_2$ concentration, the weight of the SOF and sulfate in PM captured by the filter 2 are obtained respectively.

Next, the electromagnetic valve 10 of the above gas feeder 4 is switched over to communicate the oxygen supply passage 8 with the heating furnace 1, and oxygen is fed into the heating furnace 1 through the flow controller 6. The oxygen flow at this time is measured by a flow controller 6, and the results thereof are sent to the personal computer 19 as flow signal.

In the above heating furnace 1, due to the heating of the filter 2 at 1000° C. in oxygen atmosphere, the dry soot remaining on the above filter 2 is burnt (oxidized) to generate $CO_2$ and CO (this is almost trifling in amount), which, together with oxygen, flow out to the gas flow passage 11.

The gases which flow out from the gas flow passage 11 (containing $CO_2$ and CO produced by the above combustion and other generated gases) branch through the gas flow passages 12 and 13. The gas which runs through the one gas flow passage 12 flows into the oxidation processor 14A of the oxidation reduction processor 14 through the flow meter 16. As the oxidation processor 14A is fed with oxygen, CO which is contained in the above gas is oxidized to become $CO_2$ and is mixed with the $CO_2$ in the above gas and sent to the $CO_2$ analyzer 15A of the gas analyzer unit 15 together with other gases, where the $CO_2$ concentration is measured.

The gas which runs through the other gas flow passage 13 runs into the reduction processor 14B of the oxidation reduction processor 14 through the flow meter 18. In this case, the gas is sent to the $SO_2$ analyzer 15B of the gas analyzer unit 15 without undergoing any processing and is wasted without having measurement of concentration.

From the above gas analyzer unit 15, a signal showing the $CO_2$ concentration having configuration as shown in the mark c in FIG. 3 is outputted, which is inputted into the personal computer 19. As the signal to represent the oxygen flow is inputted into the personal computer 19, based on the oxygen flow and $CO_2$ concentration, the weight of the dry soot in the PM captured by the filter 2 is obtained.

In this embodiment, in capturing PM by the filter 2, the emission G from the engine 20 is diluted. Therefor, by carrying out operation based on the weight of the dry soot, SOF and sulfate with the above dilution rate taken into account, the weight of the dry soot, SOF and sulfate in the emission can be obtained.

As described above, according to the method and apparatus for analyzing particulate matter in gas of the present invention, a filter 2 which has captured PM is accommodated in a heating furnace 1. At first, the filter 2 is heated at a predetermined temperature in an inert gas atmosphere such as nitrogen gas to gasify SOF and sulfate. The gasified SOF and sulfate are further treated for oxidation or reduction to make into $CO_2$ and $SO_2$. The concentrations are determined, and based on the concentrations the weight of SOF and sulfate in PM captured by the filter 2 is obtained. Then, the filter 2 is heated in the heating furnace 1 under oxygen atmosphere to generate $CO_2$. Based on the concentration, the weight of the dry soot in the PM captured by the filter 2 is obtained. Accordingly, it is possible to fractionate individually the dry soot, SOF and sulfate in the PM contained in the emission G from the engine 20 and measure the fractionate simply and with precision.

In the embodiment described above, the gas flow passage 11 provided on the downstream side of the heating furnace 1 is divided into equal parts 12 and 13. One gas flow passage 12 is provided with an oxidation processor 14A and $CO_2$ analyzer 15A, and the other gas flow passage 13 is provided with a reduction processor 14B and $SO_2$ analyzer 15B. As a result, the gas generated in the heating furnace 1 is divided into two equal parts, and inevitably the output signals obtainable in gas analysis becomes small. A constitution to resolve this problem is described in the second embodiment (see FIG. 5).

Figure 5:
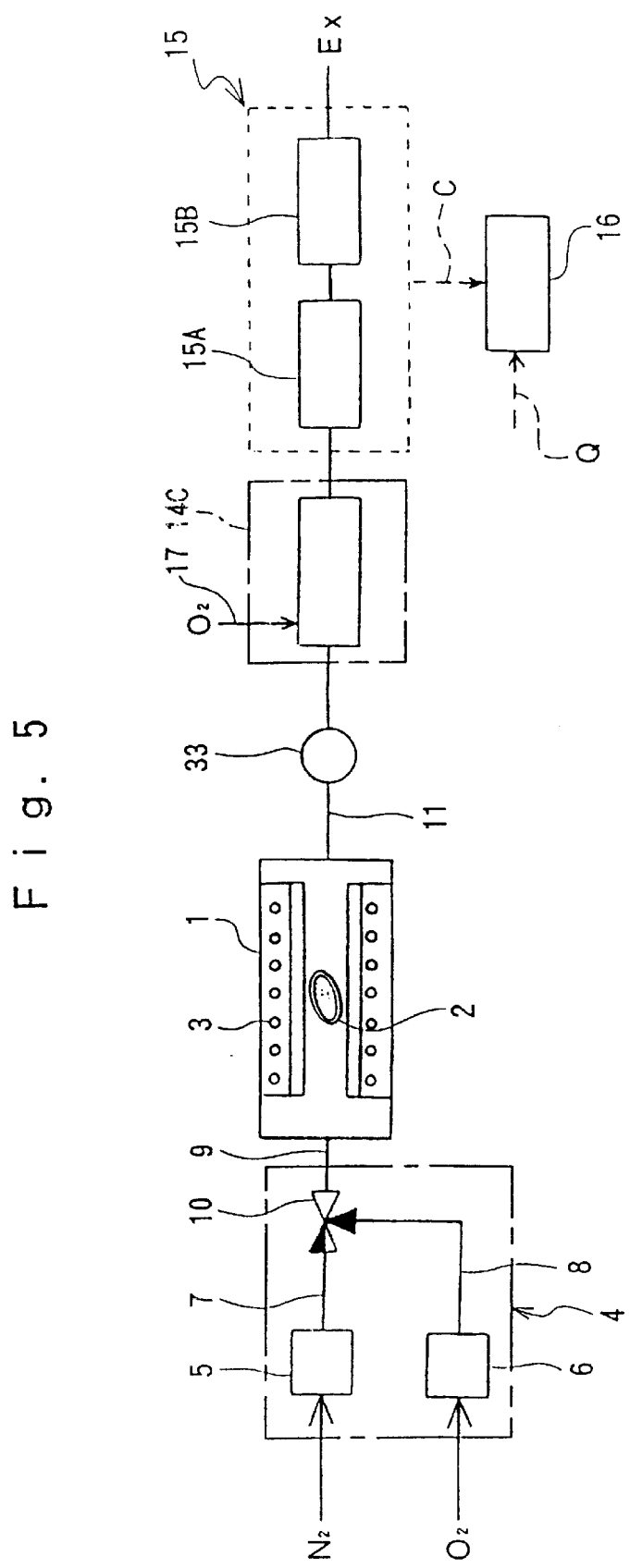
FIG. 5 is a view schematically showing another embodiment of the apparatus for analyzing the particulate matter in the gas according to the present invention.

In FIG. 5, reference numeral 33 denotes a flow meter provided in the gas flow passage 11 on the downstream side of the heating furnace 1. The flow meter 33 is similar to the flow meters 16, 18 of the first embodiment. In the oxidation reduction processor 14 provided on the downstream side of the flow meter 33, an oxidation reduction-catalyst having platinum (Pt) as the principal component is provided. An oxygen supply passage 17 is connected to the oxidation reduction catalyst. Further, in the gas analyzer unit 15 provided on the downstream side of the oxidation reduction processor 14, there are disposed in series a $CO_2$ analyzer 15A and an $So_2$ analyzer 15B.

To explain the method for analyzing the particulate matter using an analyzing apparatus of the particulate matter in the gas shown in FIG. 5 above, firstly, prior to the analysis, using a sampling apparatus shown in FIG. 2, an emission G from the engine 20 is sampled by a predetermined flow and the PM in the emission G is captured by the filter 2.

The filter 2, which has captured PM, is placed in the heating furnace 1 and heated in advance to make the inside temperature 1000° C. At first, the electromagnetic valve 10 of the gas feeder 4 is actuated to make the nitrogen gas feeding passage 7 communicate with the heating furnace 1 to feed nitrogen gas into the heating furnace 1 through a flow controller 5. The flow rate of the nitrogen gas at this time is measured by the flow controller 5, and the results thereof are sent to the personal computer 19 as the flow signal.

In the above heating furnace 1, the filter 2 is heated at 1000° C. in a nitrogen gas atmosphere, by which the SOF and sulfate in the PM captured by the filter 2 are gasified. The gasified SOF and sulfate flow out into the gas flow passage 11 along with the nitrogen gas and other gases.

The gas sent out through the gas flow passage 11 (containing the gasified SOF and sulfate) flows into the oxidation reduction processor 14 through the flow meter 33. The oxidation reduction processor 14 is supplied with oxygen, wherein the SOF out of the gasified SOF and sulfate is oxidized by the oxidation reduction catalyst and oxygen to become $CO_2$ and $H_2O$. On the other hand, the sulfate is reduced by the oxidation reduction catalyst to become $SO_2$. The $CO_2$, $H_2O$, and $SO_2$ are sent to the gas analyzer unit 15 in their state.

The gas then enters the gas analyzer unit 15, the $CO_2$ concentration is measured by the $CO_2$ analyzer 15A, the $SO_2$ concentration is subsequently measured by the $SO_2$ analyzer 15B. The $CO_2$ concentration and $SO_2$ concentration signals are outputted from the gas analyzer unit 15, and the $CO_2$ and $SO_2$ concentration signals are inputted to the personal computer 19. As the signal to represent the flow of the nitrogen gas is inputted into the personal computer 19, based on the nitrogen gas flow, $CO_2$ concentration and $SO_2$ concentration, the weight of the SOF and sulfate in PM captured by the filter 2 are obtained respectively.

Next, the electromagnetic valve 10 of the above gas feeder 4 is switched over to communicate the oxygen supply passage 8 with the heating furnace 1, and oxygen is fed into the heating furnace 1 through the flow controller 6. The oxygen flow at this time is measured by a flow controller 6, and the results thereof are sent to the personal computer 19 as a flow signal.

In the above heating furnace 1, due to the heating of the filter 2 at 1000° C. in oxygen atmosphere, the dry soot remaining on the above filter 2 is burnt (oxidized) to generate $CO_2$ and CO (this is almost trifling in amount), which, together with oxygen, flow out to the gas flow passage 11.

The gases which flow out from the gas flow passage 11 (containing $CO_2$ and CO produced by the above combustion) flow into the oxidation reduction processor 14 through the flow meter 33. As the oxidation reduction processor 14 is fed with oxygen, CO which is contained in the above gas is oxidized to become $CO_2$. The gas along with $CO_2$, is sent to the $CO_2$ analyzer 15A of the gas analyzer unit 15, where the $CO_2$ concentration is measured. The $CO_2$ concentration signal is inputted to the personal computer 19. The gas exiting the $CO_2$ analyzer 15A is sent to the $SO_2$ analyzer 15B, where it is wasted without undergoing measurement of concentration.

As the signal to represent the oxygen flow is inputted to the above personal computer 19, the weight of the dry soot in PM captured by the filter 2 is obtained based on the oxygen gas flow and the $CO_2$ concentration.

The weight of the dry soot, SOF and sulfate in the emission G can be obtained in the same manner as the first embodiment, wherein the dilution rate is taken into consideration.

As described above, according to the second embodiment as well, the dry soot, SOF and sulfate in PM contained in the emission G from the engine 20 can be individually fractionated and measured simply with precision.

In the second embodiment described above, the gas formed in the heating furnace 1 is not divided into two parts. Furthermore, the gas analyzer unit 15 is sequentially passed through the $CO_2$ analyzer 15A and the $SO_2$ analyzer 15B, so that larger concentration signals of $CO_2$ and $SO_2$ can be obtained. Also, the system has an advantage that the whole constitution of the apparatus is simplified.

In the first and second embodiments, heating of the filter 2 is first performed in the heating furnace 1 with the inert gas atmosphere at a predetermined temperature (1000° C.), but the heating may be effected by the combination of low temperature heating and the high temperature heating. The selection is explained as the third embodiment below.

The SOF contained in the emission G exhausted from the diesel engine 20 includes one originated from light oil and one originated from engine oil. The former SOF is evaporated at a relatively low temperature (e.g., about 350° C.) and the latter SOF is evaporated at a relatively high temperature (about 700° C.). In the first and second embodiments, in heating a filter 2 by introducing an inert gas atmosphere in the heating furnace 1, the filter 2 is kept at a constant temperature. Thus, it is not possible to measure by distinction between the SOF of light oil origin and the SOF of engine oil origin.

In the third embodiment, the filter 2 is heated under the inert gas atmosphere by heating the filter 2 at a low temperature to a degree that the low boiling temperature SOF is evaporated. Thereafter, a high temperature heating is preformed to a degree that the high boiling temperature SOF is evaporated. In this manner, by carrying out the heating of the filter 2 under the inert gas atmosphere at the two step temperatures of low and high levels, it becomes possible to measure the SOF of light oil origin and the SOF of engine oil origin by distinction.

With respect to the heating procedure having two steps (low and high levels) as described above, there are optional methods, for example, to change over the temperature in the heating furnace 1 by a temperature adjusting mechanism so as to heat the filter 2 first in a low temperature condition and then to heat the filter 2 in a high temperature condition, or alternatively, to provide the heating furnace 1 inside with a low temperature heating unit and a high temperature heating unit, so as to make heating in the low temperature heating unit first, and to make heating by shifting the filter 2 to the high temperature heating unit.

The present invention is not limited to the embodiments mentioned above but can be practiced by modification into various styles. For example, as a heating furnace 1, a high frequency heating furnace or an infrared image furnace may be used. As an inert gas to be supplied to the heating furnace 1, there may be used besides nitrogen gas optional gases such as argon gas.

Besides, in case of oxidizing in the oxidation processor 14A or the oxidation reduction processor 14 the gasified SOF formed in heating the filter 2 at a predetermined temperature under the nitrogen gas atmosphere, $H_2O$ is formed along with $CO_2$. The $H_2O$ may become an interference component in the measurement of $CO_2$ or $SO_2$. Accordingly, the $H_2O$ may be eliminated before it is fed to the gas analyzer unit 15. As an alternative, a gas analyzer unit may include a $CO_2$ and $SO_2$ analyzer which are not affected by the interference component.

Furthermore, the gas analyzer unit 15 may be provided with a Fourier conversion infrared spectrometer (FTIR gas analyzer unit apparatus). The FTIR gas analyzer unit apparatus is capable of simultaneously measuring with a single unit the concentration of $CO_2$ and $SO_2$ and is also capable of measuring $NO_x$ and the like. Therefor, it is possible to measure at a stroke the concentrations of other components as well as the dry soot, SOF and sulfate contained in PM. Furthermore, the gas analyzer unit 15 may be provided with a mass spectrometer (mass analyzer). The mass spectrometer is also capable of simultaneously measuring with a single unit the concentrations of $CO_2$, $SO_2$, $NO_x$ and the like. Accordingly, when the FTIR gas analyzer apparatus or mass spectrometer are provided the constitution of the entire apparatus is simplified.

As described above, in accordance to the present invention, it is possible to measure the dry soot, SOF and sulfate from the PM simply and with precision. In particular, the dry soot, SOF and sulfate, which occupy the major part in PM and which could not be measured by the conventional filter weighing method or by the procedure disclosed in publication as listed in the beginning of the present invention, can be individually fractionated to measure the concentration or weight. Furthermore, the low concentration PM can be measured with precision.

Figure 6:
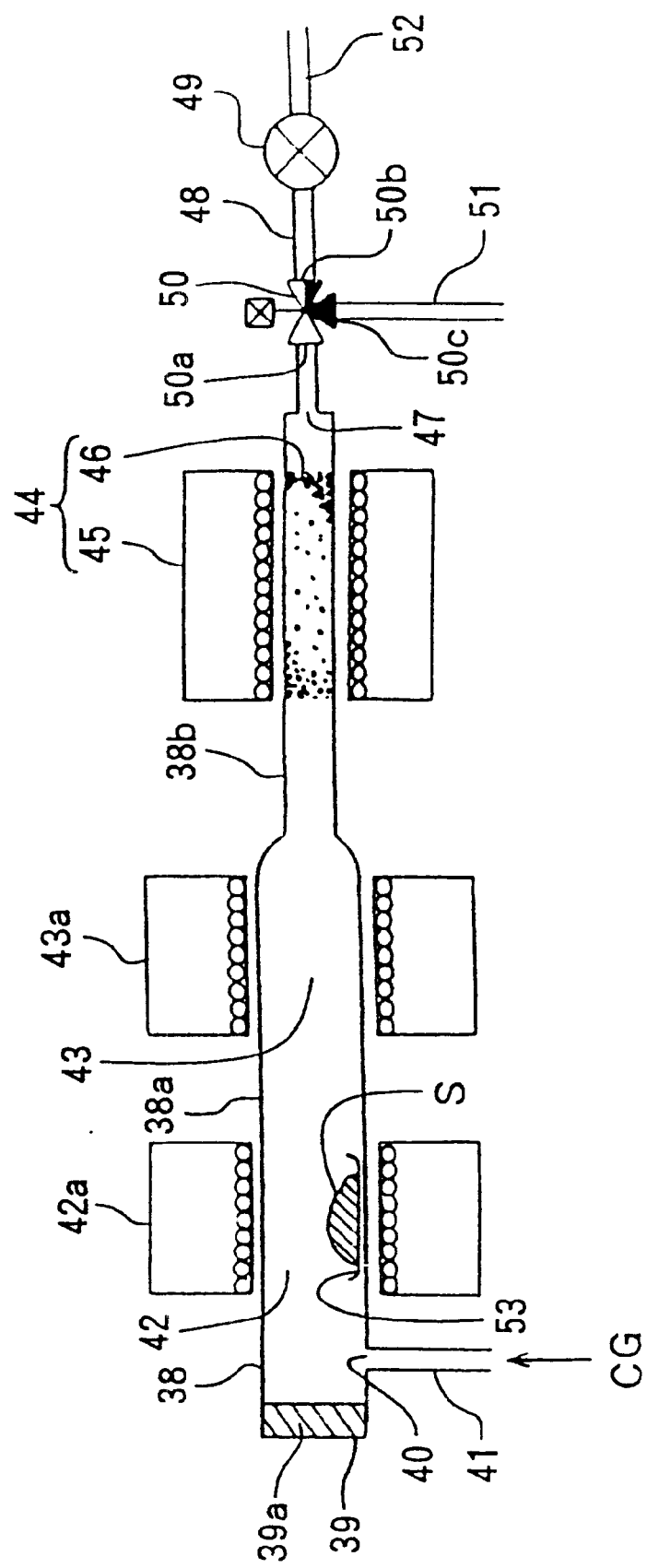
FIG. 6 is a view schematically illustrating one example of a carbon differentiating and analyzing apparatus according to the present invention.

Hereafter, the fourth embodiment of the present invention is described with reference to FIG. 6. FIG. 6 is a view schematically illustrating one example of a construction of a carbon differentiating and analyzing apparatus of the present invention. A thermal decomposition tube 38 includes, for example, a large diameter portion 38*a* and a small diameter portion 38*b*. The thermal decomposition tube 38 is made of a heat-resistant material such as quartz or heat-resistant ceramics, and its heat-resisting temperature is above 1200. A sample entrance 39 is formed on one end (the large diameter part 38*a* side) of the thermal decomposition tube, and a freely openable and closable lid 39*a* is disposed there for inserting a sample S. A carrier gas inlet 40 is disposed in the neighborhood of the lid 39*a*, and a carrier gas passageway 41 is connected to the carrier gas inlet 40. A source of inert gas such as He or $N_2$ and a source of burning-aid gas such as $O_2$ or air (not illustrated) are disposed on the upstream side of the carrier gas passageway 41, whereby either one of the inert gas and the burning-aid gas can be selectively introduced as a carrier gas CG into the thermal decomposition tube 38.

A low temperature heating portion 42 and a high temperature heating portion 43 are disposed with a suitable spacing in the large diameter portion 38*a* of the thermal decomposition tube. Heaters 42*a*, 43*a* both capable of setting an arbitrary temperature from room temperature to about 1200° C. are wound, for example, around the large diameter part 38*a*, whereby organic carbon in the sample S is evaporated in the low temperature heating part 42 and elemental carbon in the sample S is thermally decomposed in the high temperature heating part 43.

A high temperature oxidizing portion 44 is disposed in the small diameter portion 38*b* connected to the aforesaid large diameter part 38*a* and includes a heater 45 wound around the outer circumference of the small diameter part 38*b* and an oxidation catalyst 46 made of copper oxide, platinum, or the like formed in layers.

A gas exit 47 is formed on the downstream side of the small diameter portion 38*b*, and a $CO_2$ analyzer 49 made, for example, of a non-dispersion type infrared gas analyzer (NDIR) is connected to the gas exit 47 via a passageway 48. A three-way solenoid valve 50 is a switching valve disposed midway in the passageway 48 and includes a first port 50*a* connected to the gas exit 47, a second port 50*b* connected to the $CO_2$ analyzer 49 side, and a third port 50*c* connected to a gas discharging passageway 51. During normal operation (while the power is off) the gas exit 47 side and the $CO_2$ analyzer 49 are in communication with each other. A gas discharging passageway 52 is disposed on the downstream side of the $CO_2$ analyzer 49.

A sample boat 53 is used to mount the sample S thereon and is formed to have a size such that the sample boat 53 can be inserted into or taken out from the large diameter portion 38*a* through the sample entrance 39. The sample boat 53 can be slid freely in the large diameter portion 38*a*.

Next, the operation of the carbon differentiating and analyzing apparatus having the aforesaid construction will be described with reference also to FIG. 6. First, the lid 39*a* of the sample entrance 39 must be opened. At this time, in order to prevent air from flowing from the lid 39*a* side into the thermal decomposition tube 38 and to prevent $CO_2$ in the air from flowing to the $CO_2$ analyzer 49 side, the three-way solenoid valve 50 must be switched to allow the gas exit 47 and the gas discharging passageway 51 to be in communication with each other. Next, the sample S in a state of being mounted on the sample boat 53 is inserted into the thermal decomposition tube 38 so that the sample S will reach the low temperature heating part 42 which is maintained at a temperature needed for evaporation of organic carbon, for example, about 500° C. under the He atmosphere and about 300° C. under air atmosphere. Then, the three-way valve is switched to connect the gas exit 47 and the passageway 48 thereby to allow the $CO_2$ analyzer 49 and the gas exit 47 to be in communication with each other. In this state, the organic carbon is evaporated, for example, for three to five minutes. Here, if the evaporation is to be carried out under He or $N_2$ atmosphere, He or $N_2$ is introduced from the carrier gas inlet 40. If the evaporation is to be carried out under air or $O_2$ atmosphere, it is introduced also from the carrier gas inlet 40.

The organic carbon which has been evaporated by low temperature heating of the sample S in the low temperature heating part 42 is conveyed to the high temperature oxidizing portion 44 by means of the carrier gas CG. Since the high temperature oxidizing portion 44 is kept at a high temperature, for example, of 1000° C. by the heater 45, HC and CO contained in the organic carbon is oxidized into $CO_2$. The resultant $CO_2$ gas is conveyed via the three-way solenoid valve 50 by the carrier gas CG to the $CO_2$ analyzer 49, where its concentration is measured.

After the evaporation of the organic carbon is carried out for a predetermined period of time, the sample S together with the sample boat 53 is moved to the high temperature heating portion 43 which is maintained at a temperature needed in thermal decomposition of elemental carbon (for example, about 850° C). For this movement, the lid 39*a* of the sample entrance 39 must be opened. At this time, in order to prevent air from flowing from the lid 39*a* side into the thermal decomposition tube 38 and to prevent $CO_2$ in the air from flowing to the $CO_2$ analyzer 49 side, the three-way solenoid valve 50 must be switched to allow the gas exit 47 and the gas discharging passageway 51 to be in communication with each other.

Then, the sample S is heated tat the aforesaid temperature for a predetermined period of time, for example, three to five minutes in the high temperature heating part 43 for thermal decomposition. The thermally decomposed elemental carbon is conveyed to the $CO_2$ analyzer 49 via the high temperature oxidizing portion 44 by means of the carrier gas CG, in the same manner as the organic carbon. After the $CO_2$ concentration is measured in the $CO_2$ analyzer 49, the gas is discharged to the gas discharging passageway 52.

Figure 7A:
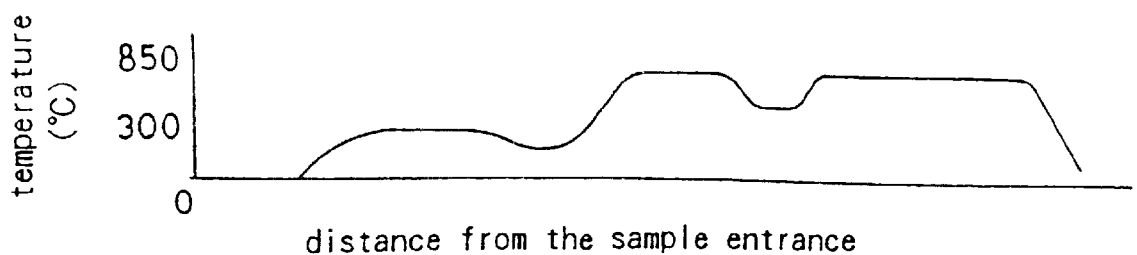
FIG. 7A is a graph schematically illustrating a temperature distribution in a thermal decomposition tube of the carbon differentiating and analyzing apparatus.

FIG. 7A is a graph schematically illustrating a temperature distribution in the thermal decomposition tube 38 of the carbon differentiating and analyzing apparatus. In the graph, the horizontal axis represents the distance from the sample entrance 39, and the vertical axis represents the temperature in the thermal decomposition tube 38.

Figure 7B:
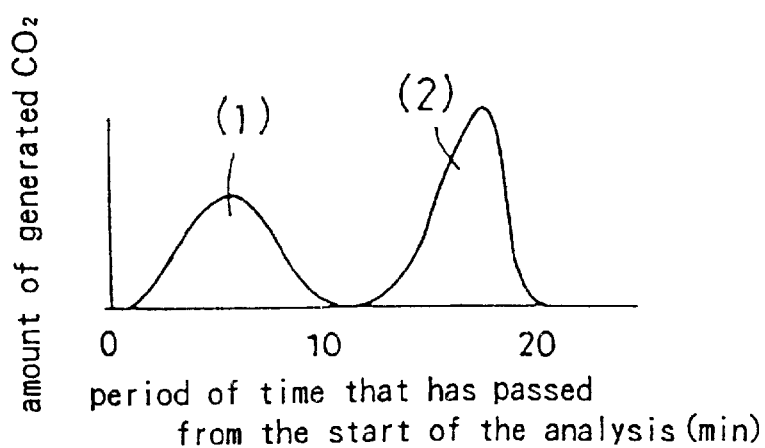
FIG. 7B is a graph schematically illustrating a result of analysis by the carbon differentiating and analyzing apparatus.

FIG. 7B is a graph schematically illustrating the amount of generated $CO_2$, which is obtained by the aforesaid carbon differentiating and analyzing apparatus. In the graph, the horizontal axis represents the period of time that has passed from the start of the analysis, and the vertical axis represents the amount of generated $CO_2$. The first peak (1) in the graph indicates the amount of $CO_2$ generated by evaporation of the organic carbon, and the next peak (2) indicates the amount of $CO_2$ generated by thermal decomposition of the elemental carbon. Thus, the amount of generated $CO_2$ respectively corresponding to the organic carbon and the elemental carbon are obtained. From these results, the amounts of the organic carbon and the elemental carbon contained in the sample S can be differentiated and analyzed.

As described above, in the carbon differentiating and analyzing apparatus of the present invention, the carrier gas inlet 40, the low temperature heating part 42 for evaporating the organic carbon in the sample S, and the high temperature heating part 43 for thermally decomposing the elemental carbon in the sample S are disposed in this order in the single thermal decomposition tube 38. Therefor, the low temperature heating portion 42 and the high temperature heating portion 43 can be simultaneously operated and each can be maintained at a respective predetermined temperature. This eliminates the need for the time required in raising the temperature or cooling in the carbon differentiation and analysis, thereby reducing the time needed for analysis.

Further, the high temperature oxidizing portion 44 for oxidizing the generated carbon compounds such as HC and CO into $CO_2$ is disposed on the downstream side of the high temperature heating portion 43 of the thermal decomposition tube 38. Therefor, even if carbon compounds such as HC and CO are mixed in the gas generated when the sample S is heated at a low temperature in the low temperature heating portion 42 and at a high temperature in the high temperature heating portion 43, these carbon compounds are oxidized with certainty in the high temperature oxidizing part 44 into $CO_2$, thereby preventing errors from being generated in the measurement performed by the $CO_2$ analyzer 49.

Figure 8:
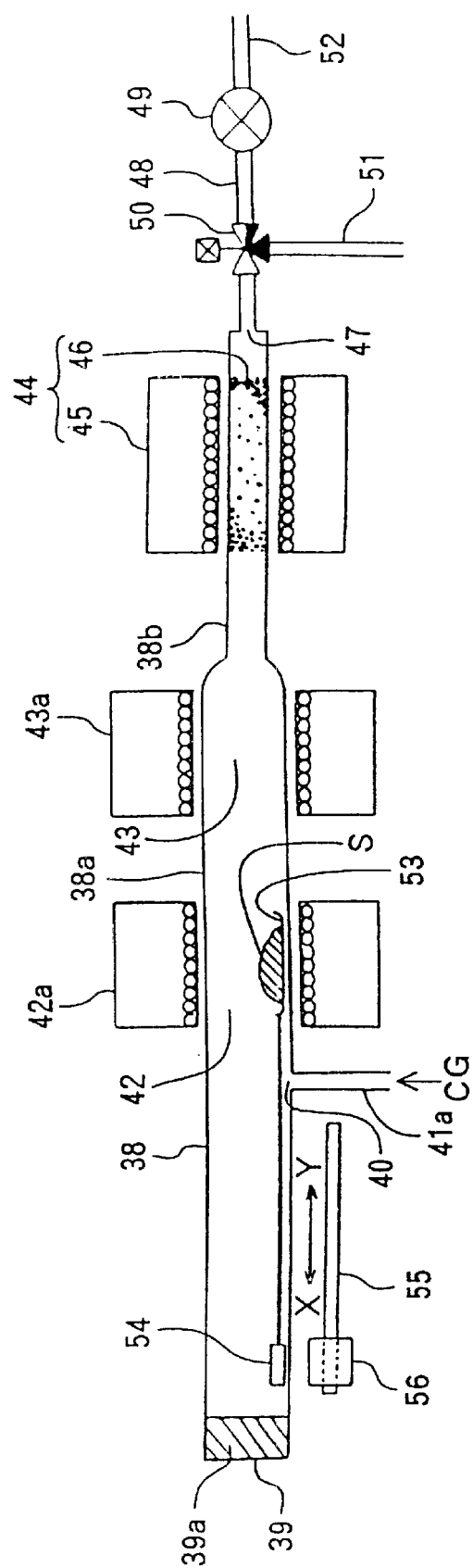
FIG. 8 is a view schematically illustrating another embodiment of the carbon differentiating and analyzing apparatus.

The carbon differentiating and analyzing apparatus of the present invention is not limited to the above embodiments alone, but can be embodied with various different modifications. For example, it is possible to adopt a construction such that, as shown in FIG. 8, an iron supporting tool 54 is connected to the sample boat 53. A guide 55 is disposed outside and below the thermal decomposition tube 38 in parallel to the thermal decomposition tube 38. A driving portion 56 made of a magnet is movably disposed in the guide 55, whereby the supporting tool 54 is moved in the direction of the arrow X or Y in FIG. 8 by the magnetic force of the magnet driving portion 56 from the outside of the thermal decomposition tube 38, instead of opening the lid 39a of the sample entrance 39 in moving the sample boat 53 having a sample S mounted thereon from the low temperature heating portion 42 to the high temperature heating portion 43. In a carbon differentiating and analyzing apparatus having this construction, the sample S can be moved in a state in which the outside air is shut off without opening the lid 39a.

Figure 9:
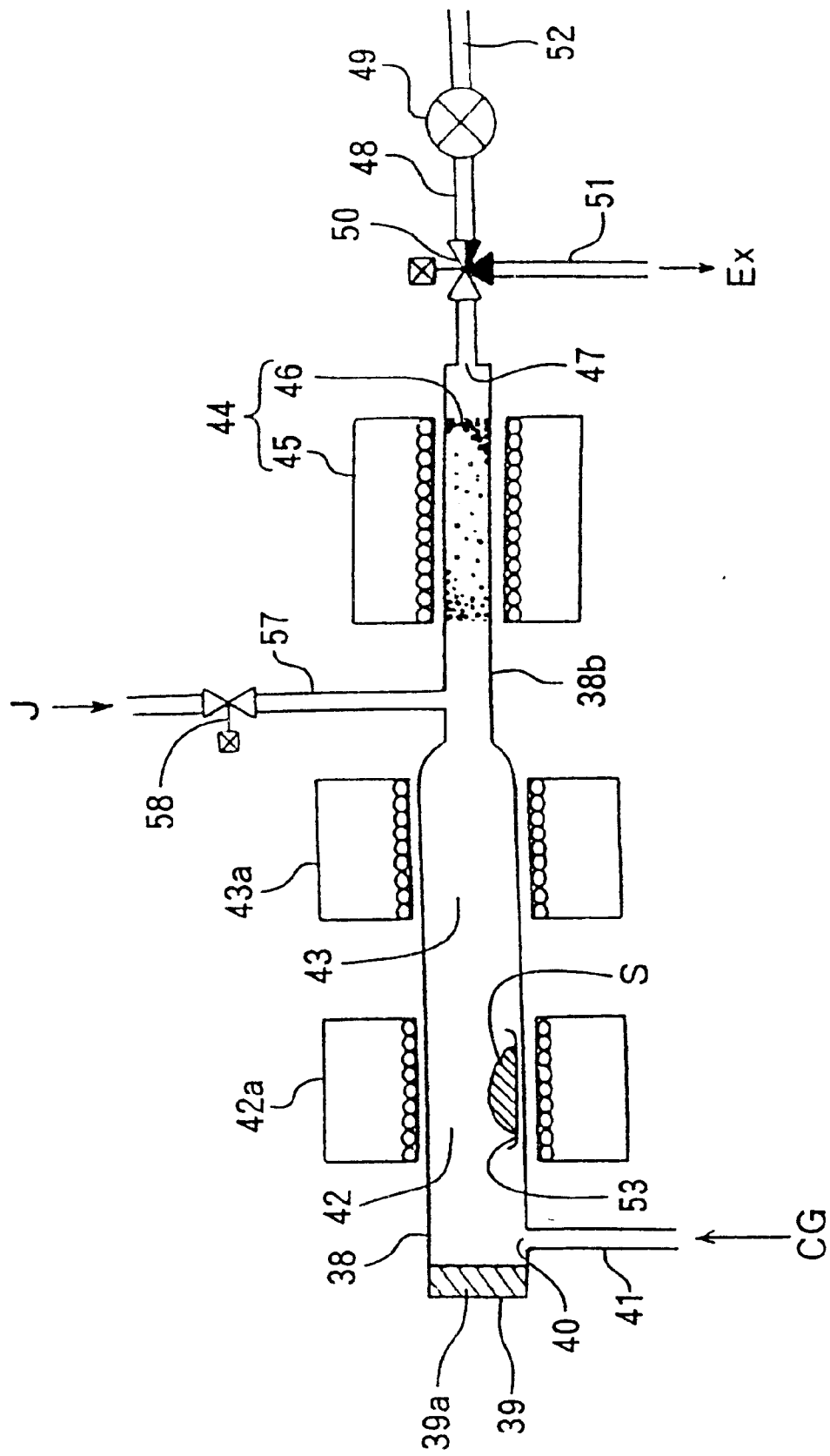
FIG. 9 is a view schematically illustrating still another embodiment of the carbon differentiating and analyzing apparatus.

Further, referring to FIG. 9, a burning-aid gas introducing tube 57 for introducing a burning-aid gas J such as oxygen or air may be connected at a site between the high temperature heating portion 43 and the high temperature oxidizing portion 44 of the thermal decomposition tube 38, whereby the burning-aid gas J is introduced into the thermal decomposition tube 38. In this case, the sample S can be burnt (oxidized) more smoothly and completely to generate $CO_2$ as desired. Here, reference numeral 58 denotes a two-way solenoid valve as an on-off valve disposed midway in the burning-aid gas introducing tube 57.

Figure 10:
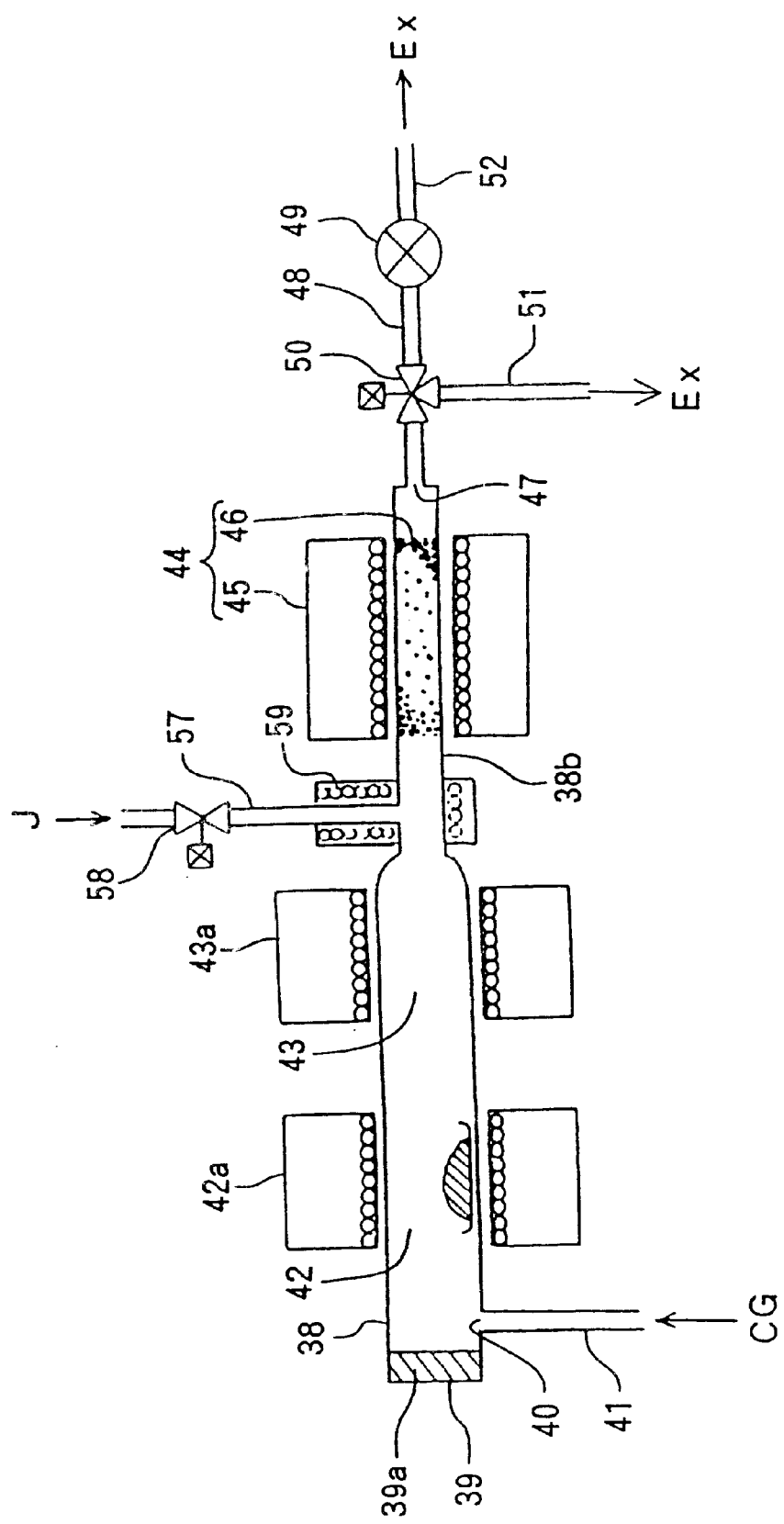
FIG. 10 is a view schematically illustrating still another embodiment of the carbon differentiating and analyzing apparatus.
Figure 11:
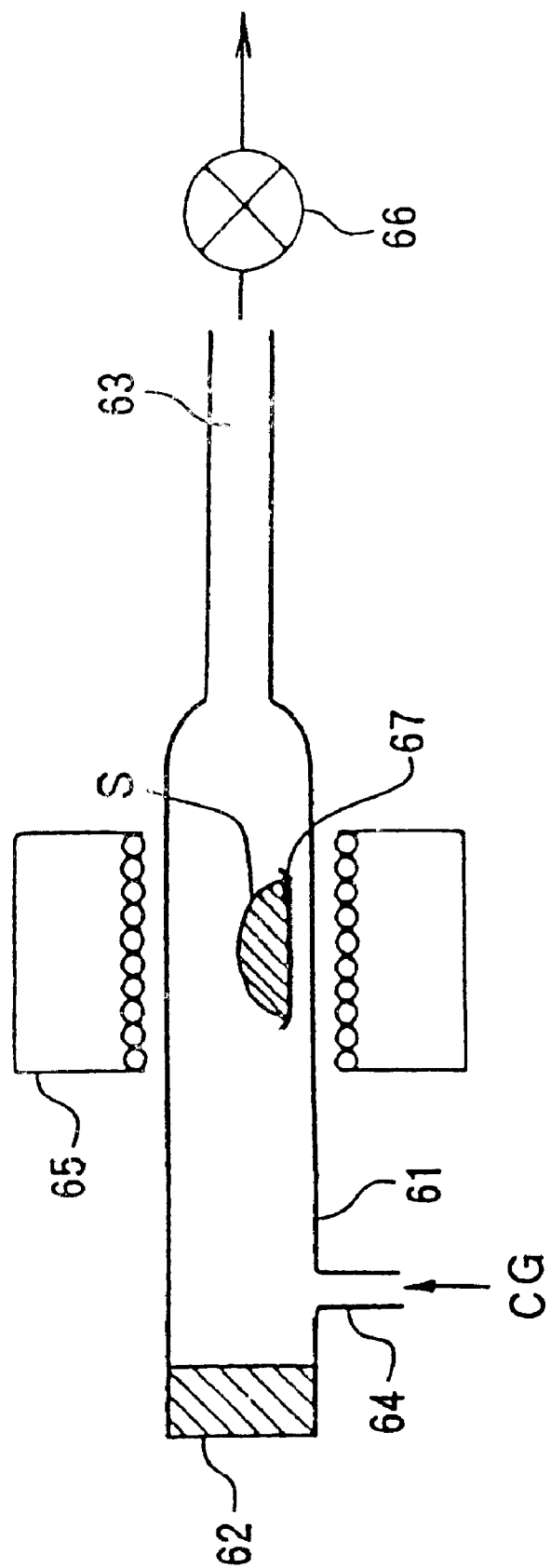
FIG. 11 is a view schematically illustrating a construction of a conventional carbon differentiating and analyzing apparatus.

Further, referring to FIG. 10, a heater 59 may be disposed in the neighborhood of the connecting portion of the burning-aid gas introducing tube 57 and the thermal decomposition tube 38, namely, in a portion of the burning-aid gas introducing tube 57 near the thermal decomposition tube 38 and in the connecting portion of the thermal decomposition tube 38, whereby the burning-aid gas J to be introduced into the thermal decomposition tube 38 may be heated in advance. In this case, the gas generated in the low temperature heating portion 42 or in the high temperature heating portion 43 will not be cooled by addition of the burning-aid gas J, so that $CO_2$ can be generated as desired.

As described above, according to the present invention, the organic carbon and the elemental carbon in a sample can be differentiated and analyzed. Further, the low temperature heating portion and the high temperature heating portion can be simultaneously operated and set at respective predetermined temperatures. This eliminates the need for the time required in raising the temperature or cooling in the carbon differentiation and analysis, thereby reducing the time needed for analysis.

Further, according to the carbon differentiating and analyzing apparatus of, HC and CO can be prevented from flowing to the $CO_2$ analyzer, thereby improving the analysis precision of $CO_2$.

Also, according to the carbon differentiating and analyzing apparatus low temperature $CO_2$ in the presence of oxygen can be completely converted into $CO_2$, thereby preventing errors of the $CO_2$ analyzer caused by the generation of CO.

Thus, according to the carbon differentiating and analyzing apparatus of the present invention, the carbon differentiation and analysis can be carried out more speedily and more accurately.

What is claimed is:

1. A method for analyzing particulate matter in a gas, comprising:
   providing a heating furnace with a filter which has captured particulate matter contained in an engine emission;
   feeding an inert gas into the heating furnace;
   heating the filter at a predetermined temperature while passing an inert gas into the heating furnace to evaporate the hydrocarbon and sulfate contained in the particulate matter;
   actuating a controllable valve attaching a gas feeder to the heating furnace thereby restricting the flow of inert gas and permitting the flow of oxygen to the heating furnace;
   oxidizing the evaporated hydrocarbon into $CO_2$ and reducing the evaporated sulfate into $SO_2$;
   analyzing the $CO_2$ and $SO_2$ with a gas analyzer unit;
   heating the filter while flowing oxygen into the heating furnace to oxidize the particulate matter remaining on the filter to have it generate $CO_2$; and
   analyzing $CO_2$ with the gas analyzer unit.

2. The method of claim 1, wherein heating the filter while flowing an inert gas into the heating furnace, further comprising:

low temperature heating to an extent that the hydrocarbon of low boiling temperature is evaporated; and high temperature heating to an extent that the hydrocarbon of high boiling temperature is evaporated.

3. The method of claim 1, wherein sulfate is passed through heated quartz fibers in reducing the evaporated sulfate into $SO_2$.

4. The method of claim 2, wherein sulfate is passed through heated quartz fibers in reducing the evaporated sulfate into $SO_2$.

5. An apparatus for analyzing particulate matter in a gas, comprising:

a gas feeder having a controllable valve attached thereto, the gas feeder and controllable valve capable of selectively feeding an inert gas or oxygen to a heating furnace;

a heating furnace for heating at a predetermined temperature a filter in an inert gas atmosphere, the filter capable of capturing the particulate matter contained in the engine emission;

an oxidation reduction processor for oxidizing or reducing the gas generated by heating; and a gas analyzer unit for determining the concentrations of $CO_2$ and $SO_2$ under supply of a gas from the oxidation reduction processor.

6. A method for analyzing particulate matter in a gas, comprising:

providing a heating furnace with a filter which has captured particulate matter contained in an engine emission, feeding an inert gas to the heating furnace containing the filter;

heating the filter at a predetermined temperature in an inert gas atmosphere to evaporate the hydrocarbon contained in the particulate matter;

controllably actuating a three-way electromagnetic valve attaching a gas feeder to the heating furnace thereby restricting the flow of inert gas and permitting the flow of oxygen to the heating furnace;

oxidizing the evaporated hydrocarbon into $CO_2$;

analyzing the $CO_2$ with a gas analyzer unit;

heating the filter while flowing oxygen into the heating furnace to oxidize the particulate matter remaining on the filter to have it generate $CO_2$; and analyzing $CO_2$ with the gas analyzer unit.

7. An apparatus for analyzing particulate matter in a gas, comprising:

a gas feeder for selectively feeding an inert gas or oxygen to a heating furnace, said gas feeder comprising an inert gas feeding passage, an oxygen feeding passage, and a connecting flow passage; said gas feeder having a three-way electromagnetic valve controllably connecting said inert gas feeding passage, said oxygen feeding passage, and said connecting flow passage;

a heating furnace for heating at a predetermined temperature a filter which has captured the particulate matter contained in the engine emission, said heating furnace heating said filter in an inert gas atmosphere;

an oxidation processor for oxidizing the gas generated by heating; and a gas analyzer unit for determining the concentrations of $CO_2$ under supply of a gas from the oxidation processor.

* * * * *